United States Patent [19]

Vecchio et al.

[11] Patent Number: 6,009,380

[45] Date of Patent: Dec. 28, 1999

[54] TECHNIQUE FOR ELIMINATING AMBIGUITY WHEN MAKING PULSE-ECHO TIMING MEASUREMENTS

[75] Inventors: Christopher J. Vecchio, Broomall; Ian E. Kibblewhite, Strafford; Donald E. Kotas, Blue Bell, all of Pa.

[73] Assignee: Ultrafast, Inc., Malvern, Pa.

[21] Appl. No.: 08/968,459

[22] Filed: Sep. 10, 1997

Related U.S. Application Data

[63] Continuation of application No. 08/850,140, May 2, 1997, abandoned
[60] Provisional application No. 60/017,013, May 3, 1996.
[51] Int. Cl.$^6$ .................. G01H 1/00; G01H 5/00
[52] U.S. Cl. .................. 702/142; 702/143; 702/149; 73/597; 73/589; 73/627; 73/761; 367/87
[58] Field of Search ............... 702/142, 143, 702/149, 189; 73/597, 589, 570, 579, 627, 629, 760, 761, 615; 367/87, 99

[56] References Cited

U.S. PATENT DOCUMENTS

| | | | |
|---|---|---|---|
| 3,918,294 | 11/1975 | Makino et al. | 73/67.2 |
| 4,294,122 | 10/1981 | Couchman | 73/761 |
| 4,363,242 | 12/1982 | Heyman | 73/761 |
| 4,471,657 | 9/1984 | Voris et al. | 73/597 |
| 4,569,229 | 2/1985 | de Halleux | 73/597 |
| 4,602,511 | 7/1986 | Holt | 73/581 |
| 4,702,110 | 10/1987 | Holt | 73/573 |
| 4,846,001 | 7/1989 | Kibblewhite | 73/761 |
| 5,031,457 | 7/1991 | Kline | 73/597 |
| 5,131,276 | 7/1992 | Kibblewhite | 73/761 |
| 5,150,620 | 9/1992 | Allison | 73/862.59 |
| 5,237,516 | 8/1993 | Heyman | 369/508 |
| 5,404,743 | 4/1995 | Froggatt | 73/7 |
| 5,493,910 | 2/1996 | Hall et al. | 73/597 |

FOREIGN PATENT DOCUMENTS

| | | |
|---|---|---|
| 0 453 650 A1 | 10/1991 | European Pat. Off. . |
| 0 589 271 A1 | 3/1994 | European Pat. Off. . |
| 20 27 333 | 1/1971 | Germany . |

OTHER PUBLICATIONS

Copy of International Search Report dated Oct. 23, 1997.

Froggat et al., "Interrupted Ultrasonic Bold Load Measurements Using the Pulsed Phase Locked Loop System," IEEE Trans. on Instrumentation and Measurement, vol. 45, No. 1 pp. 112–116 (Feb. 1996).

Bobrenko et al., "Ultrasonic Method of Measuring Stress in Parts of Threaded Joints," All Union Scientific Research Institute of Non–Destructive Testing, Kishinev, Translated from Defektoskpiya, No. 1, pp. 72–81, (Jan.–Feb. 1974).

Johnson et al., "An Ultrasonic Method for Determining Axial Stress in Bolts," A Journal of Testing and Evaluation, vol. 14, No. 5, pp. 253–259 (Sep. 1986).

G.C. Johnson, "On the Applicability of Acoustoelasticity for Residual Stress Determination," Journal of Applied Mechanics, vol. 48, No. 4, pp. 791–795 (1981).

J.S. Heyman and E.J. Chern, "Ultrasonic Measurement of Axial Stress," Journal of Testing and Evaluation, vol. 10, No. 5, pp. 202–211 (Sep. 1992).

E.P. Papadakis, Ultrasonic Velocity and Attenuation: Measurement Methods with Scientific and Industrial Applications, Physical Acoustics, vol. 12, pp. 277–297 (Edited by Mason, Warren, P., 1976).

E.P. Papadakis, "Ultrasonic Phase Velocity by the Pulse–Echo–Overlap Method Incorporating Diffraction Phase Corrections," J. Acoust. Soc., 10.6; 11.3, pp. 1045–1051 (1967).

(List continued on next page.)

*Primary Examiner*—Patrick Assouad
*Attorney, Agent, or Firm*—Ratner & Prestia

[57] ABSTRACT

A method of measuring in a material a time-of flight of a signal having a first signal burst and a second signal burst, the first signal burst having a first set of cycles and the second signal burst having a second set of cycles. The method includes identifying a cycle in the second signal burst corresponding to a cycle in the first signal burst, to measure the time-of-flight of the signal.

30 Claims, 12 Drawing Sheets

OTHER PUBLICATIONS

Gordon, Jr., B.E., "Measurement of Applied and Residual Stresses Using an Ultrasonic Instrumentation System," ISA Transactions, vol. 19, No. 2, pp. 33–42 (1980).

Komsky et al., "Ultrasonic Bridge for Simultaneous Measurements of Wave Speed and Attenuation", IEEE Ultrasonics Symposium, 1991.

Hurley et al., "Ultrasonic Velocity Measurements of Isotopically Enriched Diamonds", IEEE Ultrasonics Symponsium, 1993.

| FIG. 7A | FIG. 7B |
|---------|---------|
| FIG. 7C | FIG. 7D |

FIG. 7

| V3.0 | | | | MULTI-FREQUENCY TRANSDUCER EXCITATION | | | | | | |
|---|---|---|---|---|---|---|---|---|---|---|
| | | | | | CORRELATION | | | | | |
| REFERENCE | | | | | | | | | | |
| Zero Crossing No | 1 | 2 | 3 | 4 | 5 | 6 | 7 | 8 | 9 | |
| Use Crossing for analysis(1/0) | 0 | 0 | 0 | 0 | 1 | 1 | 1 | 1 | 1 | |
| Include Analysis in Correlation(1/0) | | | | | | 1 | 1 | | | |
| Use Crossing for Time Measurement(1/0) | 0 | 0 | 0 | 0 | 0 | 1 | | 0 | 0 | |
| Longitudinal | | | | | | | | | | |
| Time from Last Crossing | 444 | 444 | 444 | 444 | 444 | 444 | 444 | 444 | 480 | |
| Time of Zero Crossing | 444 | 889 | 1333 | 1778 | 2222 | 2667 | 3111 | 3556 | 4036 | |
| Transverse | | | | | | | | | | |
| Time from Last Crossing | 444 | 444 | 444 | 444 | 444 | 444 | 444 | 444 | 589 | |
| Time of Zero Crossing | 444 | 889 | 1333 | 1778 | 2222 | 2667 | 3111 | 3583 | 4172 | |
| MEASURED | | | | 12 | 11 | -3 | 3 | 8 | 27 | |
| | | | | 12 | 10 | -2 | 2 | -4 | -9 | |
| Longitudinal Zero Crossings | | 480 | 408 | 455 | 443 | 431 | 450 | 450 | 499 | |
| 50007/6-0kN | 163993 | 164473 | 164881 | 165336 | 165779 | 166210 | 166660 | 167110 | 167609 | |
| Transverse Zero Crossings | | 447 | 434 | 460 | 442 | 433 | 447 | 467 | 584 | |
| 50007/6-0kN | 297985 | 298432 | 298866 | 299326 | 299768 | 300201 | 300648 | 301115 | 301699 | |

FIG. 7A

TECHNIQUE FOR ELIMINATING AMBIGUITY WHEN MAKING PULSE-ECHO TIMING MEASUREMENTS

This application is a continuation application from application Ser. No. 08/850,140 filed May 2, 1997, now abandoned, which claimed priority from Provisional Application No. 60/017,013 filed May 3, 1996.

BACKGROUND OF THE INVENTION

1. Field of the Invention

This invention relates to a method for measuring the time-of-flight (TOF) of ultrasonic waves through materials, and specifically a method of identifying specific cycles in a received signal packet. The ability to identify a specific cycle eliminates a source of ambiguity in measuring the TOF of ultrasonic waves, thereby substantially improving the robustness and accuracy of systems which rely on TOF measurements.

2. Description of Related Art

There are many methods and devices which use ultrasonic waves to measure the tensile load on a load bearing member (such as a fastener).

U.S. Pat. No. 4,294,122 (to Couchman) discloses a fastener having an acoustic transducer built into its head or threaded end, and a method using the pulse echo technique to measure the pre-load stress. The method includes measuring the time for two sets of echoes to travel the length of the fastener, one set prior to pre-load and the other set during torquing of the fastener. Then, by knowing the material constant M, the grip length $\delta$, the diameter D, the parameter for correcting the stress distribution $\alpha$, and the travel time of the echoes, the stress S can be measured to obtain an accurate measure of bolt pre-load by using the following formula:

$$S = (M|(\delta + \alpha D)) \times \Delta T$$

Another patent disclosing the pulse echo time measurement technique is U.S. Pat. No. 4,471,657 (to Voris et al.). The '657 patent discloses an apparatus and method for measuring the length and stress in a load bearing member such as a fastener. The method includes measuring the time it takes two signals having the same frequency but a pre-determined phase difference to travel the length of a load-bearing member; detecting the longer of those travel times; compensating for the phase difference; and using an intelligent processing and control means to receive the time interval data and process the data to produce an accurate measure of the change in fastener length or the stress applied thereto. The apparatus includes an ultrasonic transducer permanently or temporarily in contact with the fastener.

U.S. Pat. No. 3,918,294 (to Makino et al.) describes a method of measuring axial strains applied to a bolt. An ultrasonic wave is applied to a bolt to generate forced oscillations therein and two different natural frequencies are measured in the bolt, one of which is measured when the bolt is under little or no axial force, the second of which is measured when the bolt is under axial strain. The ratio of change or the differential between the first and second frequencies is obtained and is compared to calibration data for the axial strain verses the ratio of change or differential.

Also, U.S. Pat. No. 4,569,229 (to de Halleux) teaches a method for measuring strains in load-bearing members which eliminates the need for calibration for grip length. The method comprises measuring the time an echo travels from the top of a load-bearing member to an artificial reflector and back. The artificial reflector includes vertical and horizontal boar holes or perforations in the load-bearing member. The transit time of the wave in the bolt is dependent on the stress the bolt is under.

Other stress measurement methods and devices allow the user to measure the change in stress during tightening of the load-bearing member. For example U.S. Pat. No. 4,363,242 (to Heyman) discloses using a pulsed phased-locked loop technique to measure changes in strain in a load-bearing member. The phase of a radio frequency wave is compared to the phase of a wave supplied by a continuously running voltage controlled oscillator. Then, when the load bearing member is under stress, the tension and sound velocity (which are dependent on the strain) cause an acoustic phase shift which produces a frequency shift ($\Delta F$) in the voltage controlled oscillator. The frequency shift divided by the frequency (F) is linearly proportional to the applied load. Heyman '242 displays frequency changes which are indicative of changes in the load on the bearing member. This technique requires that the ultrasonic sensor be kept on the load-bearing member during tightening and, thus, load measurement of a previously tightened load bearing member is not possible.

In contrast, several references describe methods of measuring the load on a load-bearing member which is already under tension. For example, U.S. Pat. No. 5,237,516 (to Heyman) describes a method of recertifying a load on a bearing member using a pulsed-phase, locked-loop system. The method includes comparing the phase of an ultrasonic tone burst applied to the load-bearing member (via a transducer) to the phase of a tone burst reflected through the bearing member, and adjusting a sample/hold for selecting a phase point of the reflected tone burst. The pulsed phase-locked loop system can be locked such that the phase is constant and the output frequency of the voltage controlled oscillator indicates the load applied to the bearing member. In this way the stress on a tightened bolt can be determined.

Similarly, Froggatt et al., *"Interrupted Ultrasonic Bolt Load Measurements Using the Pulsed Phase Locked Loop System,"* IEEE Trans. on Instrumentation and Measurement, Volume 45, No. 1, February 1996, pp. 112–16, describes a method of acquiring a previous phased lock point using a pulsed phase-lock loop ultrasonic system. This method focuses on analyzing the pulsed phase locked loop in the time domain rather than in the conventional frequency domain. A systematical procedure for making the measurements is described which is not dependent on the qualitative judgment of the test operator.

In addition, several references have described using time-of-flight measurements of longitudinal and shear waves to calculate tensile stress in load-bearing members. For example, Bobrenko et al., *"Ultrasonic Method of Measuring Stresses in Parts of Threaded Joints,"* All Union Scientific Research Institute of Non-Destructive Testing, Kishinev, Translated from Defektoskpiya, No. 1, pp. 72–81, January––February 1974, and Johnson et al., *"An Ultrasonic Method for Determining Axial Stress in Bolts,"* A Journal of Testing and Evaluation, Volume 14, No. 5, pp. 253–59, September 1986, describe methods for determining stresses in load bearing members by measuring the time-of-flight required for longitudinal and shear ultrasonic waves to travel up and down the length of the load-bearing members. In Bobrenko et al. and Johnson et al. the user is required to know the length of the load-bearing member in order to make a stress measurement. In both references, the stress on the bolt can be measured where only one end of the bolt is accessible.

Also, U.S. Pat. No. 4,602,511 (to Holt) teaches a method using the times of flight of both longitudinal and transverse waves to determine the stress in a load-bearing member. Both Holt and Johnson et al. do not require a stress measurement to be taken when the load bearing member is under zero stress.

As the above-discussed references indicate, the prior art is replete with references which disclose the use of piezoelectric materials embedded in or attached to load-bearing members to measure the stress in the load bearing member. Additional examples include U.S. Pat. Nos. 4,846,001 and 5,131,276 (to Kibblewhite) which describe the use of piezoelectric elements and polymers permanently attached to load-bearing members with adhesives or through a vapor deposition technique. These transducers are compatible with the above-described pulse-echo techniques used for load measurement and have the additional advantages of not having coupling induced errors, and they facilitate generation of transverse waves.

Other references of interest include G. C. Johnson, "*On the Applicability of Acoustoelasticity for Residual Stress Determination,*" Journal of Applied Mechanics, Volume 48, No. 4, 1981, pp. 791–795; and J. S. Heyman and E. J. Chem, "*Ultrasonic Measurement of Axial Stress,*" Journal of Testing and Evaluation, Volume 10, No. 5, pp. 202–211, September, 1992.

The above-discussed prior art cannot accurately measure the time-of-flight of ultrasonic waves in load bearing members. The measurement errors have magnitudes which are multiples of the period of the carrier frequency of the associated signal bursts. Ambiguity in identifying corresponding cycles between two received echo signals is the cause of this error. Errors in load determination may result particularly when the measured load changes suddenly (as when tightening with impact and impulse tools) or when techniques such as described above in Holt are used to make absolute measurements of load.

The pulse-echo-overlap method has been used to measure ultrasonic time-delay and to accurately measure the cyclic overlap and phase velocity. For example, Papadakis, Emmanuel P., *Ultrasonic Velocity and Attenuation: Measurement Methods with Scientific and Industrial Applications*, Volume 12, pp. 277–97 (Edited by Mason, Warren P., 1976) and *Ultrasonic Phase Velocity by the Pulse-Echo-Overlap Method Incorporating Diffraction Phase Corrections*, J. Acoust. Soc., 10.6; 11.3, pp. 1045–51 (1967) describe a method of measuring ultrasonic wave velocity and travel time in materials and structures. The method measures the TOF of radio frequency signal bursts in nondispersive media using an ultrasonic time intervalometer, an oscilloscope, and a transducer on a buffer rod. The correct determination is dependent on the McSkimin Δt criterion which is defined as:

$$\Delta t_m \equiv t_L - t_H = \frac{1}{f_L}\left[n - \frac{P\gamma_L}{2\pi}\right] - \frac{1}{f_H}\left[n - \frac{P\gamma_H}{2\pi}\right]$$

where $f_L$ and $f_H$ ($f_H$ is the resonant frequency ($f_R$) of the transducer) are the higher and lower frequencies differing by about 10%; P is the number of round trips between the echoes used in the measurement; $\gamma_L$ the phase shift characteristic of the specimen-transducer interface at the low frequency; $\gamma_H$ is the phase shift characteristic of the specimen-transducer interface at the high frequency; n is the number of cycles of mismatch from echo to echo; and $t_L$ and $t_H$ are the TOF values for the two frequencies. For example, $f_L$ may be about 0.9 $f_H$.

To overcome the shortcomings of not providing reliable and robust time-of-flight measurements of ultrasonic waves in materials, a method of measuring the time-of-flight of ultrasonic waves in materials is provided. An object of the present invention is to provide a method of making accurate and reliable ultrasonic tensile load measurements, for example, with impulse and impact fastener assembly tools.

SUMMARY OF INVENTION

To achieve these and other objects, and in view of its purposes, the present invention provides a method of measuring the elapsed time between receiving a first signal burst (echo) and a second signal burst (echo), including identifying corresponding cycles on the first and second signal bursts. The accurate elapsed time may be determined by measuring the elapsed time at two frequencies and calculating the difference between the two elapsed times.

In one embodiment, the method includes:

(a) identifying a cycle in said second signal burst corresponding to a cycle in said first signal burst, to measure the time-of-flight of the first signal by applying to the material a first signal having a first signal burst and a second signal burst, the first signal having a first frequency;

(b) collecting a first set of times-of-flight, relative to an arbitrary point in time, for each cycle of the first signal burst and each cycle of the second signal burst of the first signal;

(c) calculating the difference between the times-of-flight of each cycle in the first signal burst and each cycle in the second signal burst;

(d) applying a second signal at a second frequency having a third signal burst and a fourth signal burst to the material;

(e) collecting a second set of times-of-flight, relative to an arbitrary point in time, for each cycle of the third signal burst and each cycle of the fourth signal burst of the second signal;

(f) calculating second difference absolute values between the times-of-flight of each cycle in the third signal burst and each cycle in the fourth signal burst;

(e) calculating third difference absolute values between the first difference absolute values and the second difference absolute values;

(f) matching identical and similar third difference values; and (g) identifying the third difference value closest to zero.

In another embodiment, the step of identifying corresponding cycles on the first signal burst and the second signal burst includes the steps of:

(a) applying to the material a first signal, the first signal having a first portion at a first frequency and a second portion at a second frequency different than the first frequency;

(b) aligning a first zero crossing of one cycle of the first signal burst and a second zero crossing of one cycle of the second signal burst;

(c) calculating the absolute values of the differences of the zero crossings for each remaining cycle of the first signal burst and each remaining cycle of the second signal burst;

(d) summing the absolute values of the differences;

(e) successively shifting the second signal burst one cycle forward and one cycle backward relative to the alignment of the first zero crossing of one cycle of the first signal burst and the second zero crossing of the second signal burst; and (f) repeating steps (a)–(e) until the lowest cumulative zero crossing time difference of said differences.

DETAILED DESCRIPTION OF THE INVENTION

Acoustic time-of-flight (TOF) measurements are fundamental to many ultrasonic techniques. The performance of ultrasonic imaging, flaw detection, and load measurement systems is dependent upon the ability to measure the transit time of sound bursts through test media. Typically, a tone burst or impulse is transmitted into a medium and, after propagating some distance, is received after a delay in time. The signal may be received at a point other than the point of transmission or, in the case of a reflection creating an echo signal, at the point of transmission. Alternatively, the time between two echo signals can be measured. This is often done to remove stationary offsets in the measurement system. In either case, to correctly measure the time between a reference signal burst and a delayed signal burst, corresponding points or cycles on the two signal bursts must be identified. The identification of corresponding points or cycles may be difficult in the presence of noise or if the delayed signal has been distorted during propagation.

Figure 1:
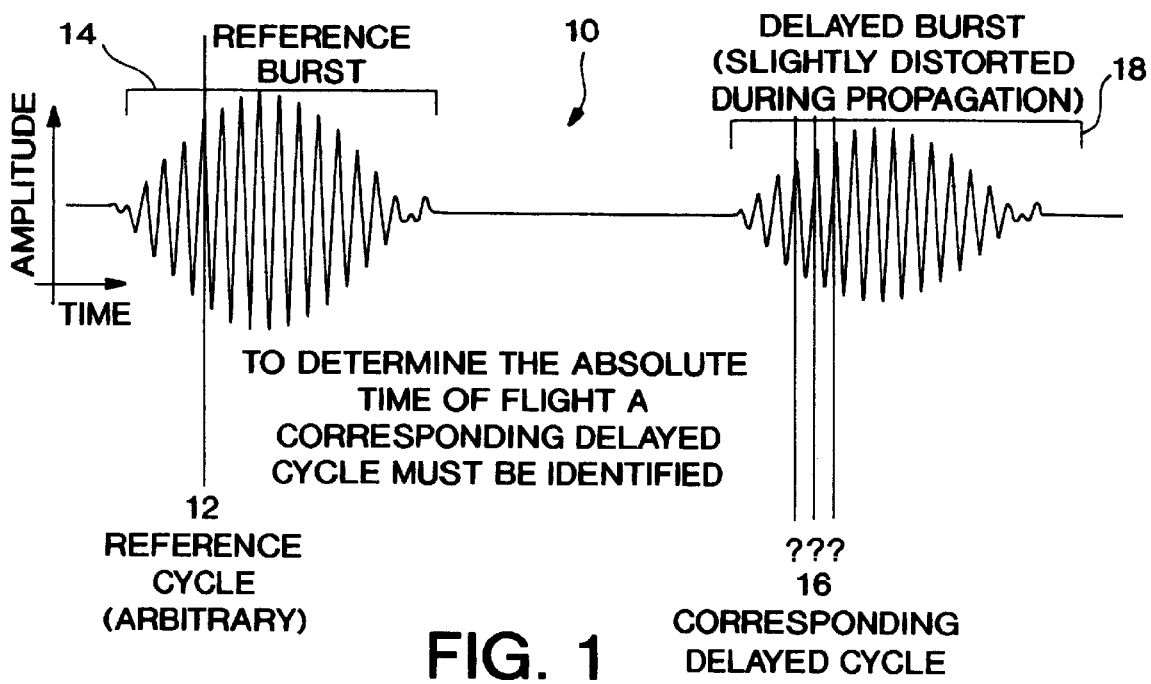
FIG. 1 is a diagram showing an arbitrary reference cycle on an arbitrary ultrasonic signal burst and potentially corresponding cycles on a delayed ultrasonic signal burst. The two signal bursts could, for example, be successive echoes generated and then received by an ultrasonic transducer from within a fastener.

FIG. 1 is a graph showing a set of two signals 10 consisting of an initial reference signal burst 14 followed in time by a delayed signal burst 18. A reference cycle 12 may be arbitrarily chosen from the cycles comprising the initial burst. The corresponding cycle on the delayed burst is not readily identifiable although general potential candidates may be identified. The delayed signal burst 18 was slightly distorted during propagation. In general, if the signal 10 is of narrow bandwidth, a mistake in identifying corresponding cycles will be a gross error equal to an integral number of cycles at the carrier frequency. The question marks in FIG. 1 represent the ambiguity in identifying the cycle of the delayed signal burst 18 corresponding to the reference cycle 12 on the reference burst 14.

Figure 2:
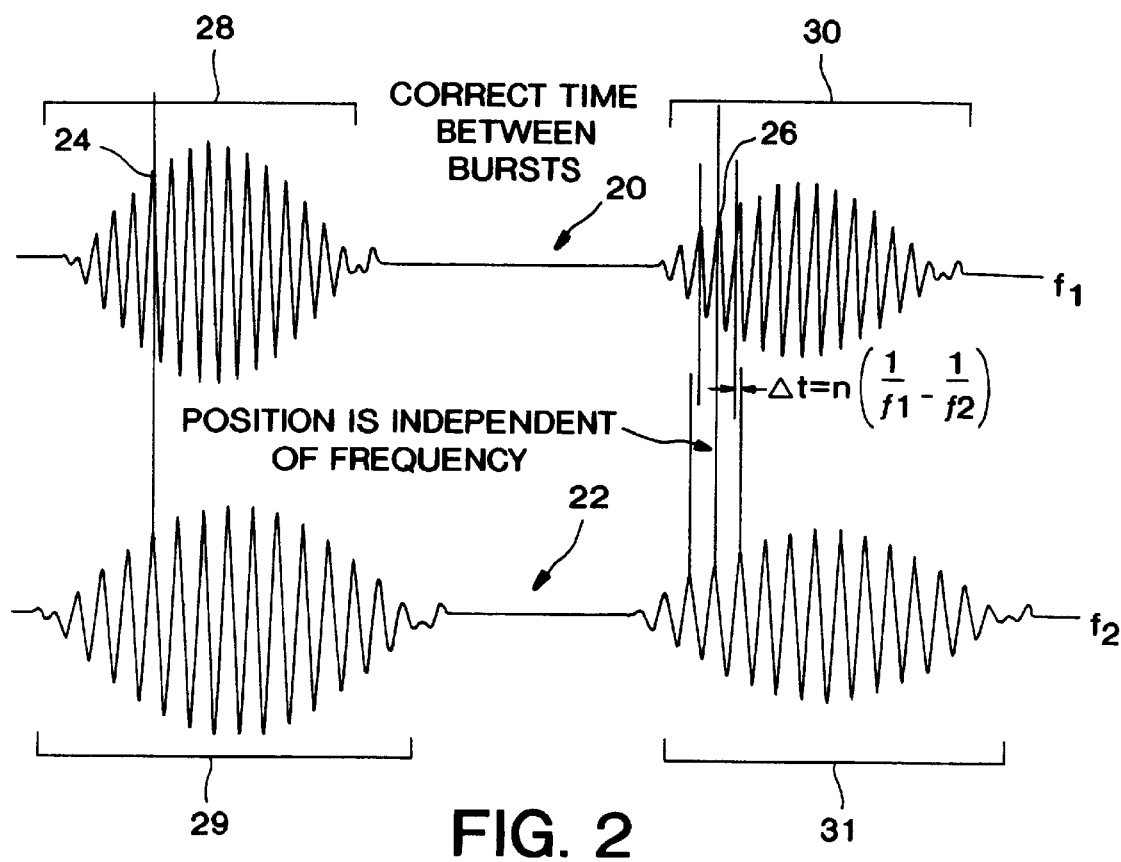
FIG. 2 is a diagram showing two sets of signal bursts having different frequencies $f_1$ and $f_2$, and the change in elapsed time, $\Delta t$, between the pair of signals at $f_1$ and the pair at $f_2$.

FIG. 2 is a diagram showing two sets of signals 20 and 22 having slightly different carrier frequencies $f_1$ and $f_2$, respectively. The ambiguity in identifying corresponding cycles on two signal bursts 28 and 30 of one signal set 20 may be resolved by measuring the elapsed time or TOF between the signal bursts first at one frequency $f_1$ and then measuring the elapsed time between signal bursts 29 and 31 of a second signal at frequency $f_2$, which is different from frequency $f_1$. If corresponding cycles 24 and 26 on bursts 28 and 30, respectively, are chosen correctly, then the time between cycles 24 and 26 will not change with frequency. If the corresponding cycles on two bursts are chosen incorrectly, however, the elapsed time will change when the frequency is shifted. The change in elapsed time, $\Delta t$, (also known as McSkimin $\Delta t$) between receiving signal 20 and receiving signal 22 is equal $$\Delta t = n\left(\frac{1}{f_1} - \frac{1}{f_2}\right)$$

where $f_1$ and $f_2$ are the two carrier frequencies and n is the error in cycles.

In one embodiment, the present invention is directed to a method of automating the above described method set forth in Papadakis, and more specifically in utilizing the above-identified simplified McSkimin $\Delta t$ equation for an automated process. Essentially, the present invention verifies that the TOF measurement of signals 20 and 22 is independent of frequency as the correct transit time should be. In practice, the frequency shift $(f_1-f_2)$ should be large enough to make $\Delta t$ recognizable above the system's inherent timing noise but small enough to eliminate dispersive effects. That is, the frequency shift $(f_1-f_2)$ should be small enough to ensure that the system and propagation time delays are assumed to be independent of frequency. The procedure described above forms the core of an algorithm known as the "minimum differences algorithm." The algorithm is particularly suitable for automated TOF measurement.

To use the "minimum differences algorithm," TOF data relative to an arbitrary point in time (such as the time the initial burst is transmitted) are collected for each cycle in an initial burst and for each cycle in a subsequent burst. The data are collected at two or more frequencies. Once the data have been collected, a list of potential TOF values is generated for each frequency by calculating the time difference between each cycle in the subsequent signal burst and each cycle in the initial signal burst for the two signals at different frequencies. The TOF data lists for each frequency are then compared to each other, and similar or identical TOF values from each list are matched. The matched TOF values are independent of frequency. Then, the matched TOF values are compared to an estimate of an absolute TOF value. An estimate of the absolute TOF may be obtained through measuring the time between the initial signal burst and the subsequent signal burst by identifying a cycle in the subsequent signal burst close in relative amplitude to the reference cycle in the initial signal burst. This estimate need only be accurate within a few cycles. The matched TOF values closest to the estimated absolute TOF will be the correct TOF values. Following this method, the cycle on the subsequent signal burst corresponding to the reference cycle on the initial signal burst can be identified. In this manner, the ambiguity in identifying the correct cycle in a subsequent signal burst is eliminated and absolute TOF measurements can be made.

A series of example calculations follows which are related to the minimum differences algorithm/multifrequency technique. A typical tone burst consists of at least 16 cycles. The cycles at the beginning and end of the signal bursts contain frequencies other than the fundamental frequency. If included in the calculations, these other frequencies can obscure the results. (There is an implicit assumption that we are operating at two distinct frequencies.) Also, if we were to apply the minimum differences algorithm to all of the cycles, the number of computations would be quite large: $(16 \times 16) \times (16 \times 16) = 65536$ subtractions. For these reasons we typically work only with 9 cycles from the center of the bursts (ignoring the first 4 and the last 3 cycles) and we eliminate from the second round of subtractions any time-of-flight values that are more than a few cycles away from a reasonable estimate of the true TOF value. Even so, the number of calculations prohibits the presentation of a "full" example on paper. Below are the actual times-of-flight data (the 9 cycles from the center of each of the four signal bursts as shown in FIG. 2) acquired from a bolt.

Time-of-Flight (TOF) Measured in $10^{-10}$ Seconds

| L1 15MHz "A" | L2 15MHz "B" | L3 18.5MHz "C" | L4 18.5MHz "D" |
| --- | --- | --- | --- |
| 265090 | 522588 | 264002 | 522126 |
| 265759 | 523255 | 264542 | 522667 |
| 266421 | 523920 | 265081 | 523205 |
| 267093 | 524587 | 265621 | 523745 |
| 267756 | 525252 | 266160 | 524284 |
| 268427 | 525919 | 266700 | 524824 |
| 269088 | 526585 | 267240 | 525364 |
| 269760 | 527252 | 267778 | 525905 |
| 270422 | 527916 | 268319 | 526443 |

Possible TOF values are formed by subtracting the time-of-flight values of each cycle in signal burst 28 (List of L1 values above) from the time-of-flight values for each cycle in signal burst 30 (List of L2 values above) for the first signal 20 at frequency $f_1$ (for example, at 18.5 MHz); and then subtracting the time-of-flight values of each cycle in signal burst 29 (List of L3 values above) from the time-of-flight values for each cycle in signal burst 31 (List of L4 values above) for the second signal 22 at frequency $f_2$ (for example, at 15 MHz). See FIG. 2. That is, possible TOF values are of the form (B–A) or (D–C), where A is any value from column "L1" above, B is any value from column "L2" above, D is any value from column "L4" above, and C is any value from column "L3" above. In order to search for the TOF values which are independent of frequency, all the (B–A) values must be compared with all the (D–C) values. Every reasonable combination of the form:

$$(B-A)-(D-C)=E$$

should be calculated and the combinations generating the minimum E values selected.

As mentioned above, the number of calculations can be reduced somewhat by ignoring TOF values which are more than a few cycles away from a reasonable estimate. For example, the (B–A) value (527916–265090) need not be included in the (B–A)–(D–C) calculations because it is far from any reasonable TOF value. The beginning of one burst obviously doesn't match up with the end of another. The minimum E values should all correspond to roughly the same TOF. The minimum E values for the above listed A, B, C, and D values are as follows:

Minimum E Values (523920–266421) – (522667–265081) = –87
(523920–265759) – (522667–264542) = 36
(524587–265759) – (523205–264542) = 165
(525919–268427) – (525364–267240) = –623
(525919–267756) – (525364–267240) = 39
(525919–269088) – (525364–267240) = –1293
(526585–268427) – (266160–524284) = 34
(526585–269088) – (266700–524284) = –87

From these calculations you can see that the minimum differences E are clustering around –87, 36, and 165. As expected, these values differ by about 126 which can be checked by using the above simplified McSkimin formula:

$$\Delta t = 1 \times \left( \frac{1}{15 \times 10^6} - \frac{1}{18.5 \times 10^6} \right) = 126 \times 10^{-10} \text{ Seconds}$$

Figure 3:
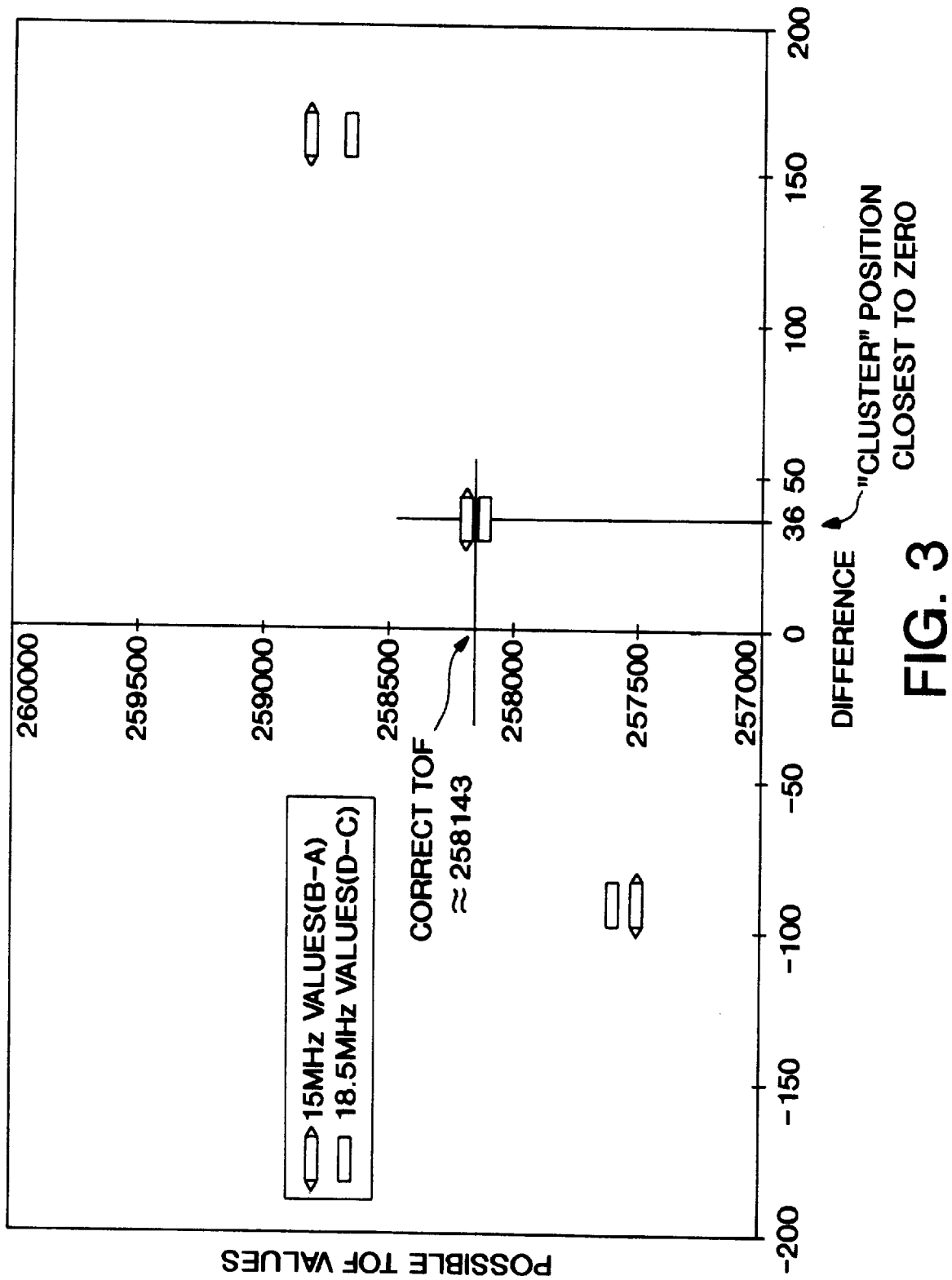
FIG. 3 is a graph of the possible correct time-of-flight (TOF) values versus the differences for each value L2–L1, minus each value L4–L3, and showing a correct TOF and minimum difference for the TOF values.

Since 36 is closest to zero, the TOF values clustering around this difference would be chosen as the correct ones. If all of the reasonable combinations are calculated and the TOF values used in each combination are plotted versus the resulting difference, the attached graph shown in FIG. 3 will be generated.

As discussed above, in its preferred embodiment, the technique according to the present invention is used in conjunction with ultrasonic load inspection techniques (such as those described above in U.S. Pat. No. 4,602,511 to Holt) for the determination of the load in fasteners. In such a configuration, the general knowledge of a fastener's geometry, material, and application (i.e., information which describes a large group of fasteners of a particular type) would be sufficient to determine the load. In contrast with the systems described in Froggatt and Heyman '516 (discussed above), no information specific to the individual fastener would be necessary in order to inspect an installed fastener.

Also, in a preferred embodiment, the technique is implemented in an algorithm suitable for automation. Papadakis, Emmanuel P., *Ultrasonic Velocity and Attenuation: Mea-* surement Methods with Scientific and Industrial Applications, Volume 12, pp. 277–97, at page 280 (Edited by Mason, Warren P., 1976), states that the "pulse-echo-overlap" method, which is similar to the technique described herein, "has never been automated and probably cannot be." The "pulse-echo-overlap" method described in the Papadakis references identifies the delayed cycle corresponding to the reference cycle by superimposing the signal bursts on top of each other by use of an oscilloscope.

The use of the present invention with transducers such as those described in the above-described Kibblewhite references also yields advantages over the prior art. For example, the thin film transducers described in the '276 patent are permanently affixed to fasteners without the use of any coupling medium and possess extremely wide frequency response characteristics. These features eliminate the need to compensate for the influence of coupling media and transducer resonance when making TOF measurements. Considerable complexity is introduced into the "pulse-echo-overlap" technique described above in the Papadakis references by the need to compensate for these influences. When used in conjunction with wide bandwidth transducers such as those described in the above Kibblewhite references, the present invention sets forth a method by which the number of variables in the McSkimin algorithm are reduced. For example, the right side of each parenthetical expression in the McSkimin algorithm discussed above is eliminated, leaving the above simplified McSkimin equation.

It is understood that the ultrasonic signals used in the present invention can be transmitted and received with electromagnetic and piezoelectric transducers, and lasers.

The instant technique also provides advantages when ultrasonically measuring load using impact and impulse tools. The sudden increases in load which occur when tightening load-bearing members with these tools can cause sudden changes in ultrasonic time-of-flight readings. The discontinuities in the TOF measurement may cause errors in load determination which can be eliminated by maintaining a constant cyclical reference.

The instant invention covers the use of this technique for the purpose of enhancing the ability to make ultrasonic time-of-flight measurements. It includes, but is not limited to, systems which measure the change in the time-of-flight of sound waves and which correlate this change to the change in tensile load in a material. It also includes but is not limited to systems which make use of changes in both longitudinal wave and transverse wave time-of-flight values to determine load. The present invention also covers situations in which accurate timing measurements may be used to measure distances such as with ranging methods and apparatus; flaw detection in materials; ultrasonic imaging; and other applications. By identifying corresponding cycles between two signal bursts, time measurements may be made which are significantly more accurate than preceding methods and devices. The reliability and accuracy of ultrasonic tensile load measurements is substantially enhanced by using the technique outlined herein.

In another embodiment according to the present invention, multiple frequency excitation is combined into a single burst to allow the use of a greater difference in the two frequencies without cycle ambiguity in identifying the corresponding measurement cycles.

In the above-described embodiments, two separate pairs of excitation bursts of slightly different frequency were used to resolve the ambiguity in detecting a specific received echo cycle. In those embodiments, technique according to the present invention assumes that the effect of ultrasonic wave propagation variations at the different frequencies on zero-crossing times is small in comparison with the difference between the waveform periods at the different frequencies. The difference between the two frequencies can be increased in order to improve the level of confidence in determining the correct cycle but only to a limited extent.

In the previously described embodiments, if the time between two cycles, one cycle on each of two signal bursts is the correct time-of-flight (TOF) between those bursts, this time value will be independent of the frequency of the signal bursts. Conversely, if the two points are not on corresponding cycles, the time between the points will vary based on frequency. The difference between the time values at two different frequencies will be $$\Delta t = n\left(\frac{1}{f_1} - \frac{1}{f_2}\right)$$

where n is the error in cycles and $f_1$ and $f_2$ are the two frequencies. It can be seen that the greater the difference between $f_1$ and $f_2$, the greater the sensitivity to a mismatch of cycles. It is therefore desirable to maximize the difference between the two frequencies when using the described technique.

Figure 4:
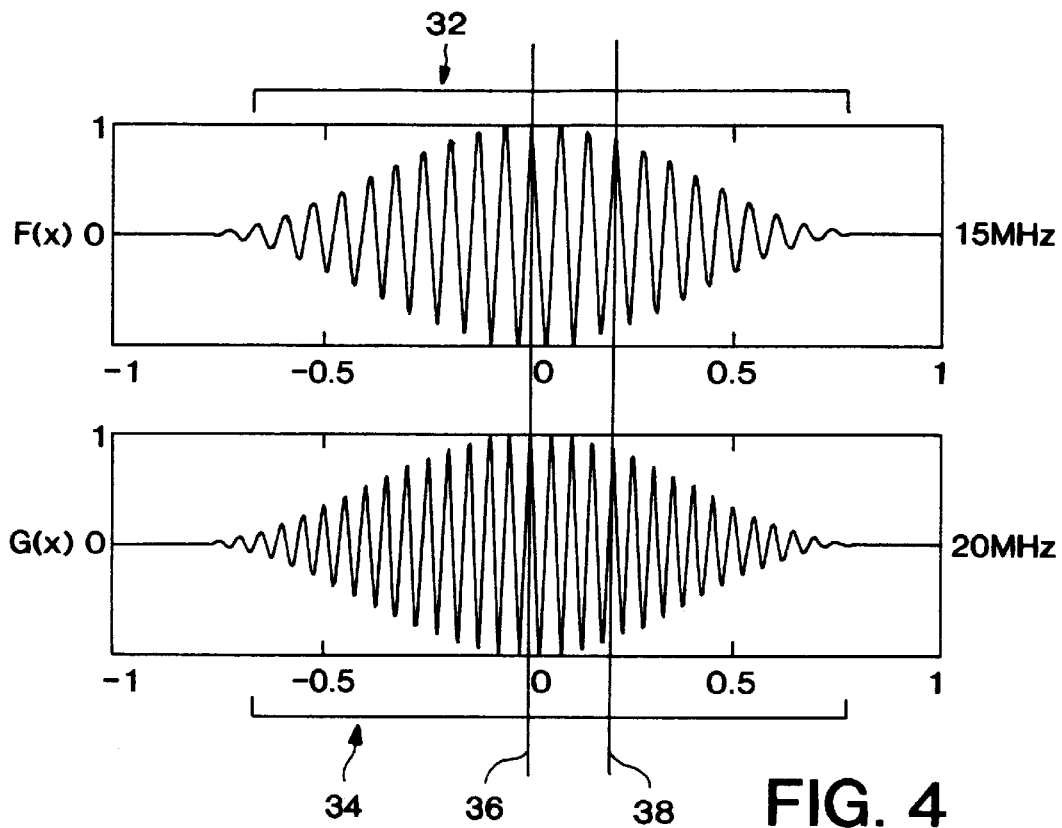
FIG. 4 is a diagram showing a first signal burst at a frequency of 15 MHz and a second signal burst at a frequency of 20 MHz, and the corresponding cycles of each signal burst.

Ambiguity in TOF measurements can be reintroduced, however, if the two frequencies are such that an integer number of cycles of the first signal burst is equal to (or approximately equal to) an integer number of cycles of the second signal burst as in FIG. 4. In FIG. 4, a first signal burst 32 is at a frequency of 15 MHz, and a second signal burst 34 is at a frequency of 20 MHz.

Figure 5:
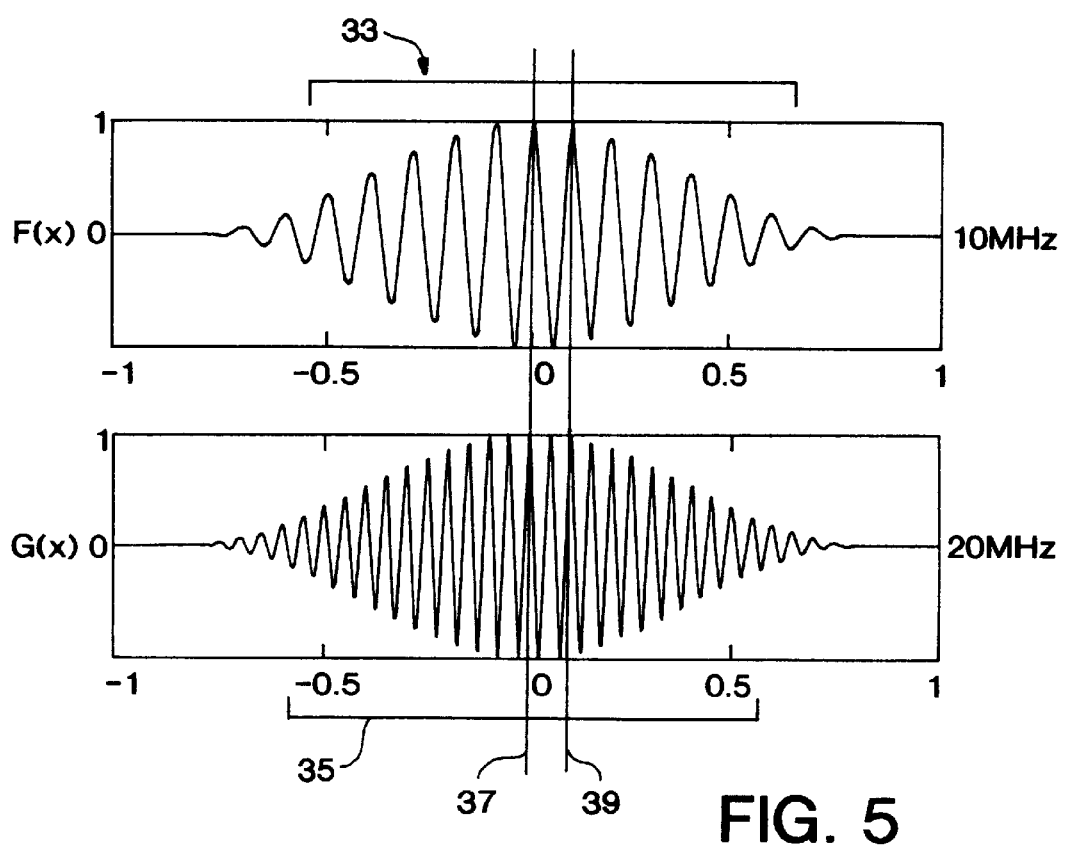
FIG. 5 is a diagram showing a first signal burst at a frequency of 10 MHz and a second signal burst at frequency of 20 MHz, and the corresponding cycles of each signal burst.

In this situation, corresponding cycles of signal bursts 32 and 34 linked by line 36 are independent of frequency. But, because 3 cycles at 15 MHz equals 4 cycles at 20 MHz, corresponding cycles linked by line 38 are also independent of frequency. If the TOF corresponding to this cycle mismatch is sufficiently far from a reasonable estimate of the correct TOF, this second solution can be confidently ignored. In certain cases, however, the secondary solutions can destroy the benefits of the technique. In FIG. 5, a worst case scenario is presented. In FIG. 5, a first signal burst 33 is at a frequency of 10 MHz and, a second signal burst 35 is a frequency of 20 Mhz. In this situation, corresponding cycles of signal bursts 33 and 35 linked by line 37 are independent of frequency. But, because 1 cycle at 10 MHz equals 2 cycles at 20 MHz, corresponding cycles linked by line 39 are also independent of frequency. In this case though, because two cycles at one frequency will be equal to one cycle at the other frequency, no advantage can be realized.

Unfortunately, when measuring load in bolts using a pulse-echo technique, propagation variations can be sufficient to reduce the level of confidence in selecting the correct cycles for the time-of-flight measurements. The purpose of His enhanced technique is to overcome the limitations described above and allow the use of multi-frequency excitations with a greater difference in frequency.

In the technique which is the subject of this embodiment according to the present invention, a single dichromatic or multi-chromatic signal burst is used instead of separate signal bursts. The approach effectively uses a change in frequency (or time between zero-crossings) to mark specific cycles in the waveform.

In one embodiment (shown using square waves for illustration purposes in FIGS. 6a–6c), the excitation burst (or reference waveform) comprises eight cycles of 20 MHz followed by eight cycles of 15 MHz. Determination of the corresponding cycles in the reference waveform and the received waveform can be done using a standard correlation technique which effectively shifts one waveform in time and compares the two waveforms to determine the best alignment.

Figure 6A:
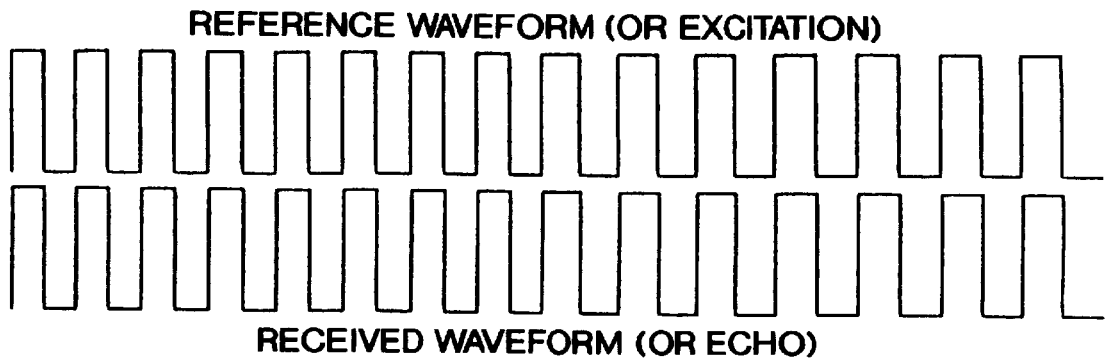
FIG. 6a is a diagram showing time-of-flight zero crossings of a pair of square waveforms and indicating the correct alignment of the waveforms.
Figure 6B:
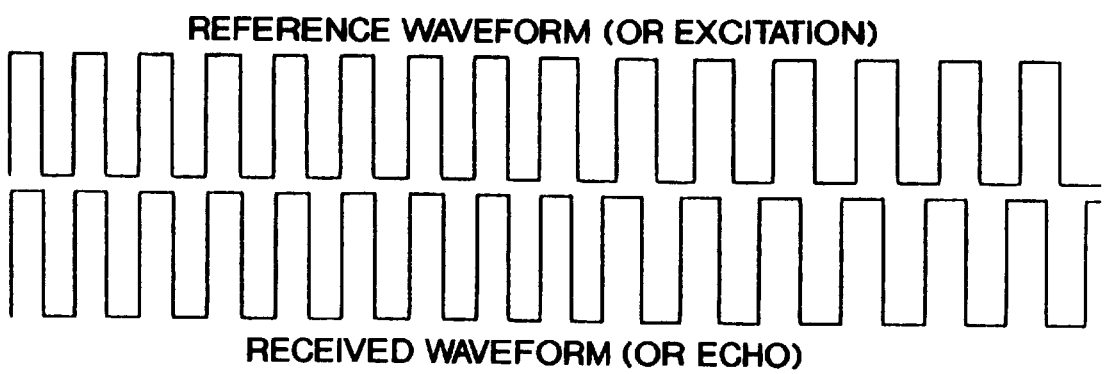
FIG. 6b is a diagram of the waveforms in FIG. 6a showing time-of-flight zero crossings and indicating that the waveforms are incorrectly aligned by +1 cycle.
Figure 6C:
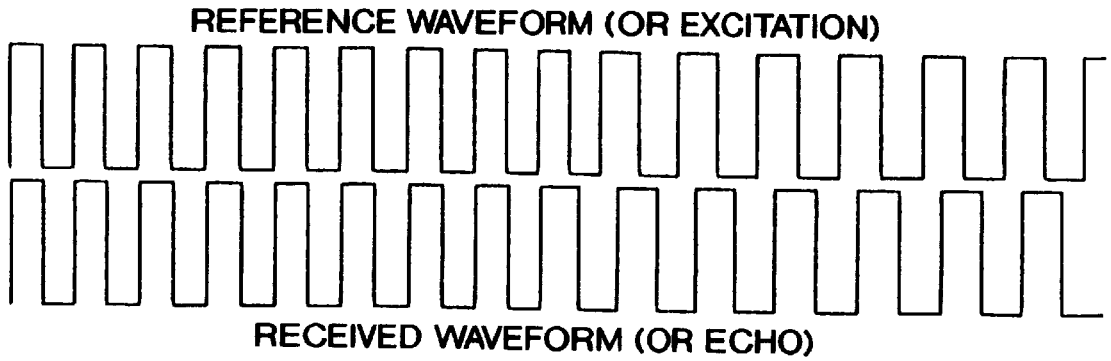
FIG. 6c is a diagram of the waveforms in FIG. 6a showing time-of-flight zero crossings and indicating that the waveforms are incorrectly aligned by −1 cycle.

For example, using a simple comparison of zero-crossings for the pairs of square-wave waveforms in FIGS. 6a–6c, it is clear that the comparison in FIG. 6a shows the correct correlation between the waveforms, and that both pairs of waveforms in FIGS. 6b and 6c are out of alignment by one cycle in each direction, that is +1 cycle and −1 cycle, respectively. Note that the reference waveform used for the correlation may be either the excitation waveform itself, or, preferably, a typical or expected received waveform which incorporates acoustic propagation and transducer response effects.

Although ultrasonic pulse-echo waveforms are typically sinusoidal, rather than square waves as shown, a simple zero-crossing comparison technique can be used for correlation. By successively aligning one zero crossing and summing the absolute value of the difference in times of the other zero-crossings, the correct alignment can be identified as the alignment which gives the lowest cumulative zero-crossing time difference.

A multiple frequency excitation waveform without discontinuities at the frequency transitions can be produced by dividing down a high frequency clock. In one embodiment, a 120 MHz clock is digitally divided by 6 to produce 20 MHz and by 8 to produce 15 MHz. High speed digital techniques are employed to ensure that the switch between the source frequencies occurs with zero phase shift.

Alternatively, an excitation burst of more than two frequencies, a continuously variable frequency (such as a "chirp" for example) or alternatively switching between two frequencies could also be used to implement this technique.

Figure 7B:
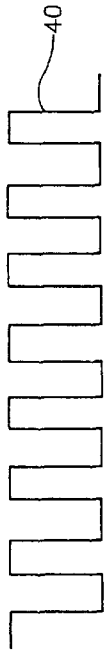
FIG. 7 is a spreadsheet showing an example of a multi-frequency excitation correlation calculation, and related graphs and tables.
Figure 7C:
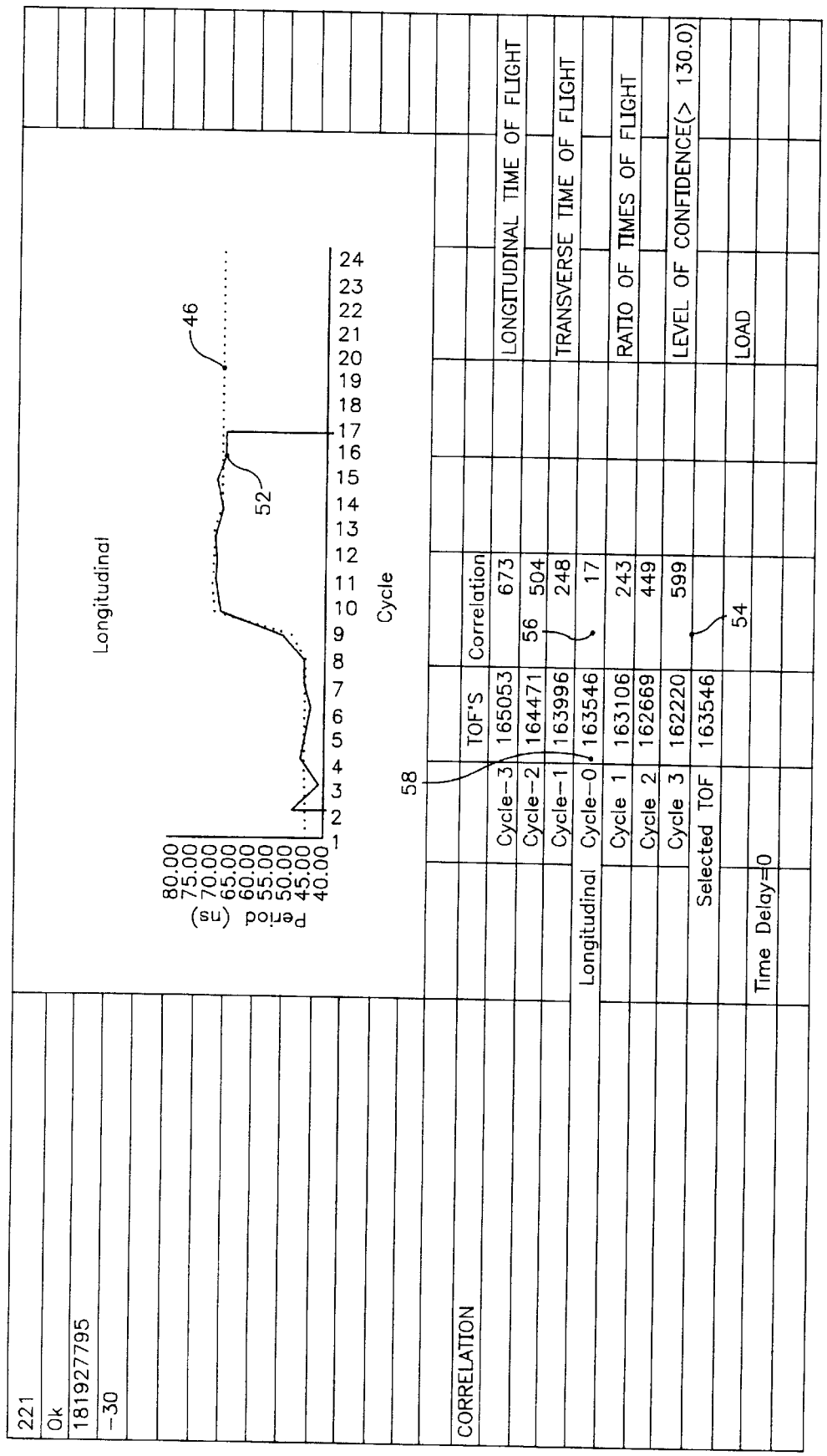
Figure 7D:
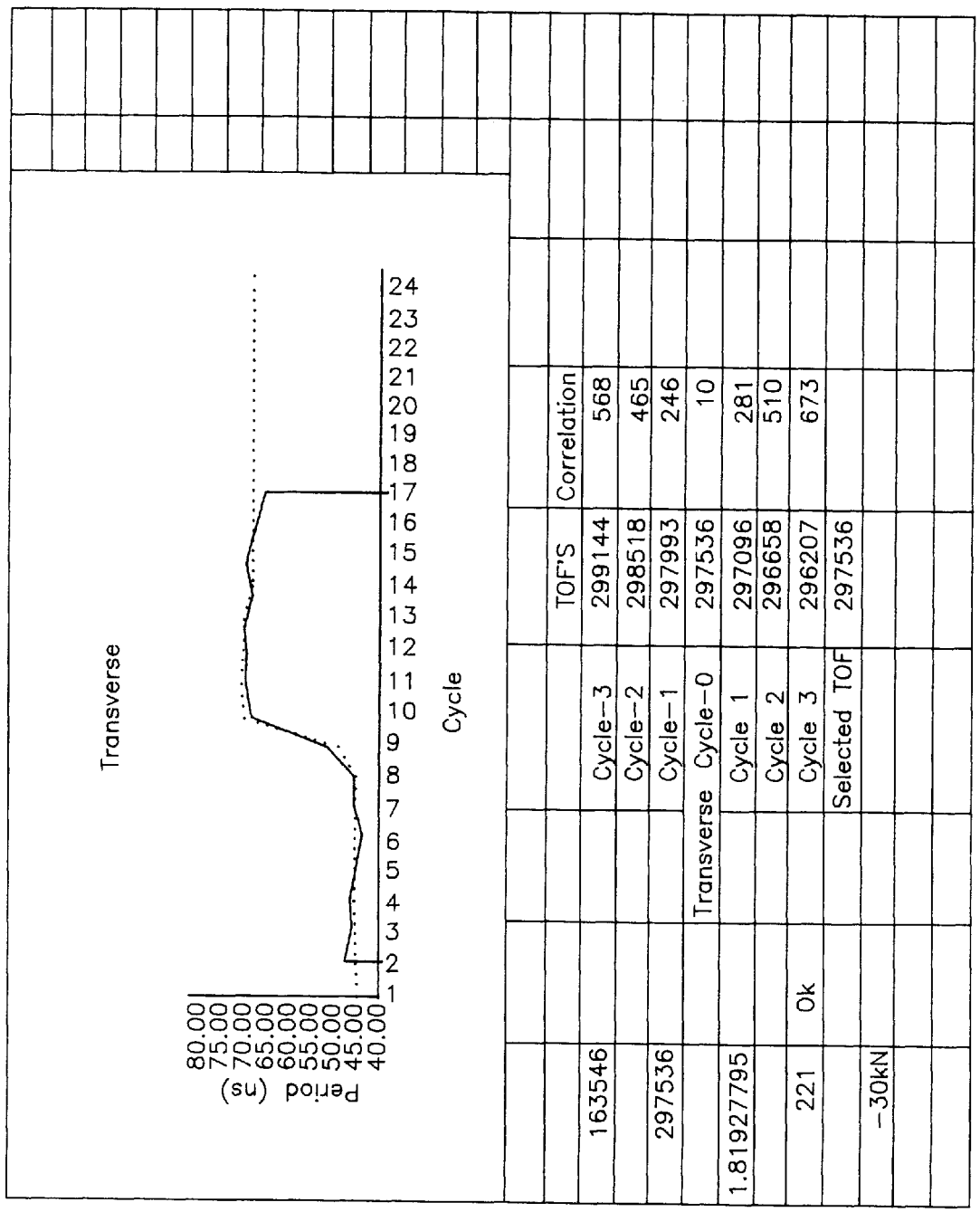

One method of identifying corresponding cycles on each waveform according to this embodiment of the present invention is shown in the spreadsheet attached hereto as FIG. 7. Two different identical waveform analyses, longitudinal and transverse, are shown with eight cycles of 22.5 MHz followed by eight cycles of 15 MHz. Only the longitudinal acoustic wave analysis will be described for illustration purposes, although in FIG. 7 a similar analysis is shown for the transverse wave.

In this method, the reference waveform 40, has reference time-of-flight zero-crossings 42, with corresponding times between time-of-flight zero-crossings 44, which are also shown graphically as curve 46. The received waveform has time-of-flight zero-crossings 48, with corresponding times between time-of-flight zero-crossings 50, also shown graphically as curve 52. A "correlation table" 54 is produced by summing the absolute values of the differences in cycle zero-crossing times over a specified number of cycles after the received waveform has been shifted in time so that one zero-crossing of the reference waveform exactly corresponds to one of the received waveform. A relative correlation index 56 for this alignment position (Cycle 0) is then computed. The received waveform is then effectively shifted in time successively a cycle in each direction and correlation indices computed for each alignment position (Cycle −3 through Cycle 3 shown in the correlation table 54 in FIG. 7). The alignment position with the lowest correlation index (in this case Cycle 0) is the correct alignment. Consequently, the shift in time to achieve this alignment is the correct time-of-flight (TOF) 58 for this pulse-echo measurement.

Correlation index 56 is computed, for example, by summing the absolute values of the time-of-flight zero crossings 48 minus the time-of-flight for the signal burst minus the reference time-of-flight 42 over a range of cycles in the middle of the burst.

In general, the Cycle 0 correlation index is calculated by:

$$\text{Correlation(Cycle 0)} = \sum_{I=m}^{n} \left| t_{of}\text{Crossing}(I) - t_{of}\text{burst(Cycle 0)} - \text{Reference Crossing}(I) \right|$$

where m is several cycles in from the beginning of the burst and n is several cycles in from the end of the burst. The time-of-flight for the burst is the calculated time of the leading edge of the first cycle in the burst and can be determined by subtracting the reference time of flight 42 for a particular cycle from the measured time of flight 48 for the cycle.

For example, the correlation index 56 appearing in the correlation table 54 of FIG. 7 is the sum of two correlations as follows:

$$\text{Correlation(Cycle 0)} = \frac{Cor1(\text{Cycle 0}) + Cor2(\text{Cycle 0})}{10}$$

where $$Cor1(\text{Cycle 0}) = \sum_{I=5}^{13} \left| t_{of}(I) - t_{of1}\text{burst(Cycle 0)} - ref(I) \right|$$

$$Cor2(\text{Cycle 0}) = \sum_{I=5}^{13} \left| t_{of}(I) - t_{of2}\text{burst(Cycle 0)} - ref(I) \right|$$

The $t_{of}(I)$ is the measured time-of-flight 48 for cycle I, ref(I) is the reference time-of-flight 42 for cycle I, and $t_{of1}$burst (Cycle 0) and $t_{of2}$burst(Cycle 0) are time-of-flights for the burst Cycle 0 computed in the following way:

$t_{of1}$burst(Cycle 0)=$t_{of}$(6)−ref(6)

$t_{of2}$burst(Cycle 0)=$t_{of}$(7)−ref(7)

where $t_{of}$(6) and $t_{of}$(7) are measured time-of-flights 48 for cycles 6 and 7, and ref(6) and ref(7) are the reference time-of-flights 42 for cycles 6 and 7. The time-of-flight 58 for Cycle 0 appearing in the correlation table 54 is the average of the above two burst time-of-flights and is calculated as follows:

$$t_{of}\text{burst(Cycle0)} = \frac{t_{of1}\text{burst(Cycle0)} + t_{of2}\text{burst(Cycle0)}}{2}$$

For example, $t_{of1}$burst(Cycle 0)=166210−2667=163543

$t_{of2}$burst(Cycle 0)=166660−3111=163549 yielding, $$t_{of}\text{burst(Cycle 0)} = \frac{163543 + 163549}{2} = 163546$$

-continued $$Cor1(\text{Cycle }0) = |165779 - 163543 - 2222| +$$
$$|166210 - 163543 - 2667| +$$
$$\vdots$$
$$\vdots$$
$$|170315 - 163549 - 6771|$$
$$= 95$$

$$Cor2(\text{Cycle }0) = |165779 - 163543 - 2222| +$$
$$|166210 - 163543 - 2667| +$$
$$\vdots$$
$$\vdots$$
$$|170315 - 163549 - 6771|$$
$$= 74$$

$$\text{Correlation}(\text{Cycle }0) = \frac{95 + 74}{10} = 17$$

Similarly, the equations for Cycle +1 are as follows:

$$Cor1(\text{Cycle }+1) = \sum_{I=5}^{13} \left| t_{of}(I-1) - t_{of1}\text{burst}(\text{Cycle }+1) - ref(I) \right|$$

$$Cor2(\text{Cycle }+1) = \sum_{I=5}^{13} \left| t_{of}(I-1) - t_{of2}\text{burst}(\text{Cycle }+1) - ref(I) \right|$$

where $$t_{of1}\text{burst}(\text{Cycle }+1) = t_{of}(5) - ref(6)$$

$$t_{of2}\text{burst}(\text{Cycle }+1) = t_{of}(6) - ref(7)$$

With this invention, the frequency difference can be increased as required, subject only to the practical limitations of the ultrasonic transducer and acoustic wave propagation, in order to minimize the ambiguity in determination of the correct cycle and therefore provide a high level of confidence in measuring the correct pulse-echo time-of-flight.

There are two alternative embodiments of this invention which were not included in the provisional patent application but which should be included in the application we are preparing now.

Figure 8:
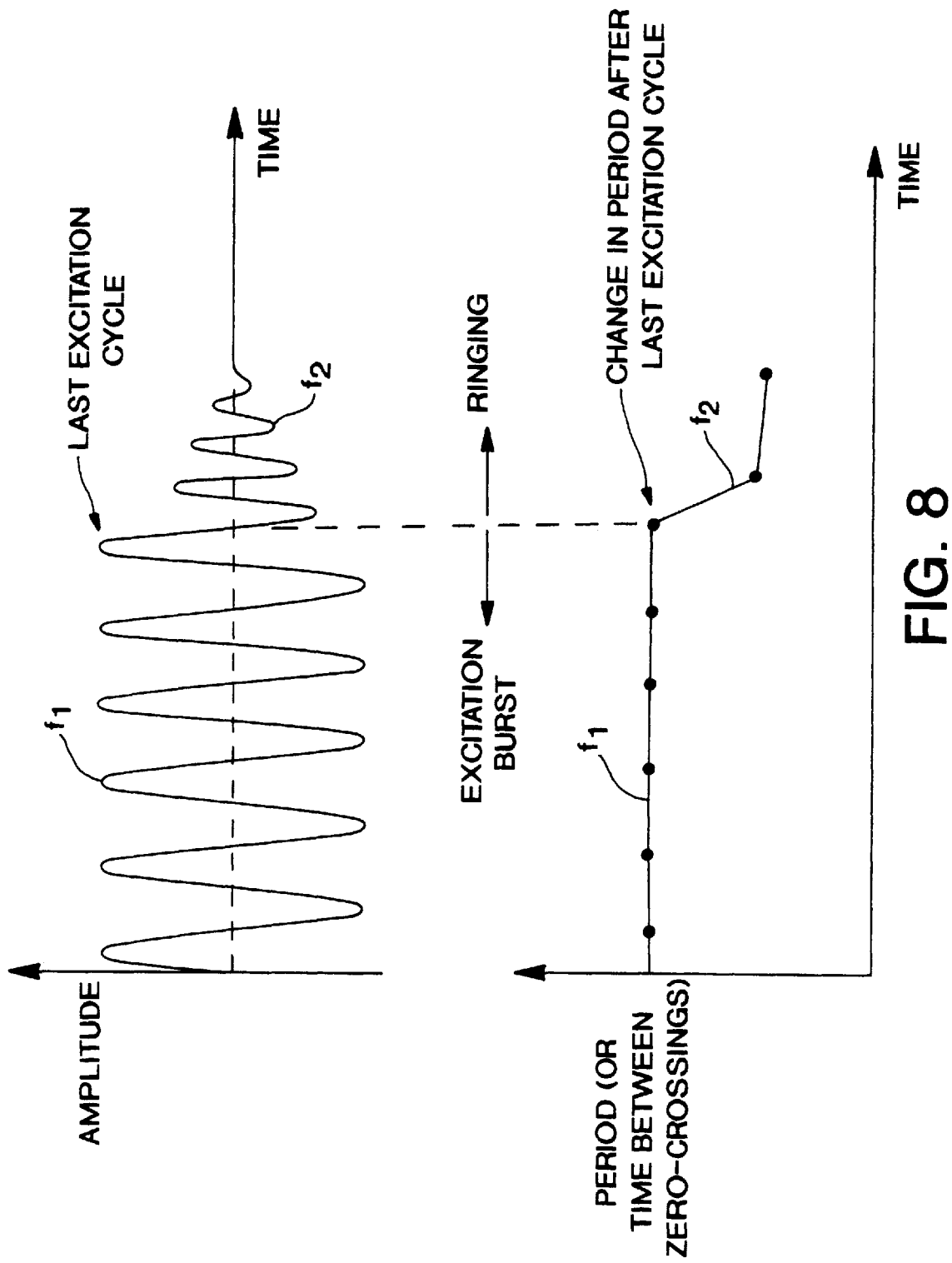
FIG. 8 is a diagram showing a signal burst at a first frequency $f_1$ and a second frequency $f_2$ equal to the transducer/drive resonant frequency, where $f_2$ is less than $f_1$, and a graph showing the period or time between zero crossings versus time for each frequency.

In an alternative embodiment of the present invention, the resonant frequency of the transducer, drive and connected electrical circuitry provides the second frequency with the above-described multi-frequency pulse-echo technique. Immediately after a transducer excitation burst, a transducer will oscillate or "ring" at its fundamental resonant frequency for a few cycles. If the excitation frequency is chosen to be slightly different from the resonant frequency, a change in frequency or period (time between zero-crossings) can be detected during these few ringing cycles, as shown in FIG. 8. Consequently, it is possible to identify the cycle which was the last excitation cycle from this decrease (as shown in the FIG. 8) or increase in the time between zero-crossings as in the previous embodiment but using a single frequency excitation.

In the above embodiments, the same excitation frequencies are used to produce the acoustic waves for both the longitudinal and transverse wave measurements. This is often necessary since the transducers are usually capable of operating efficiently in only a very narrow frequency range. Because of the different speeds-of-sound of the longitudinal and transverse ultrasonic waves (ratio of longitudinal speed/transverse speed is approximately 1.83 in steel), the two waves generated with excitation at the same frequency have different wavelengths and consequently different waveform diffraction or beam spread. In making measurements of the ratio of speeds-of-sound based on pulse-echo times-of-flight of these two wave types, it is desirable to have waves with similar diffraction characteristics in order to ensure that the time measurements are made over identical acoustic path lengths. Consequently, selection of frequencies to optimize the propagation of each of the two wave types individually can improve the accuracy of the measurements.

Figure 9:
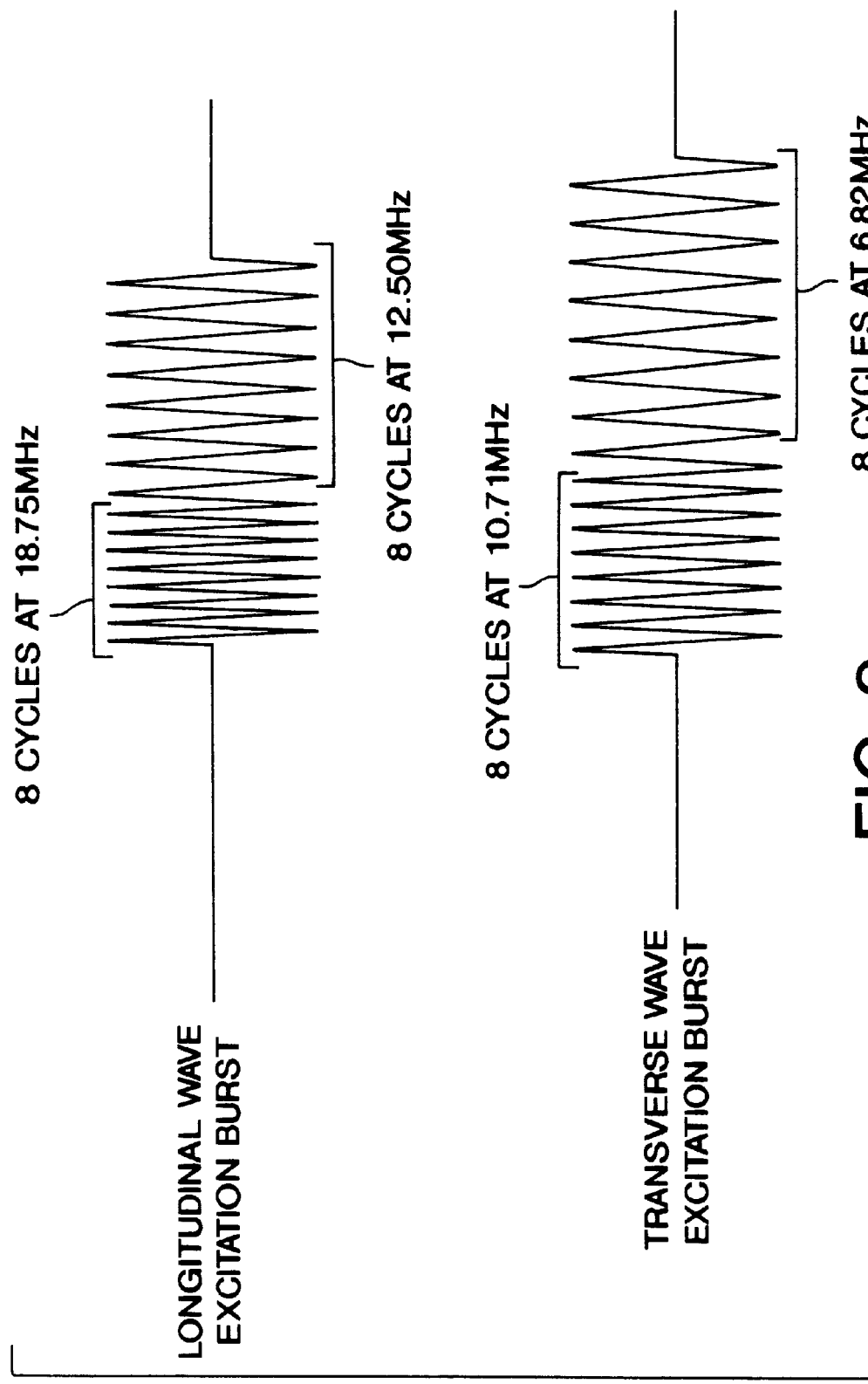
FIG. 9 is a diagram of a longitudinal wave excitation burst having 8 cycles at 18.75 Mhz, and 8 cycles at 12.5 Mhz; and a transverse wave excitation burst having 8 cycles at 10.71 MHz and 8 cycles at 6.82 MHz.

In one preferred embodiment, the frequencies are chosen so that the wavelengths of the longitudinal and transverse waves are the same in the material in which the speed-of-sound measurements are being made. FIG. 9 shows a longitudinal wave excitation burst having 8 cycles at 18.75 MHz followed by 8 cycles at 12.5 MHz, and a transverse wave excitation burst having 8 cycles of 10.71 MHz and 8 cycles at 6.82 MHz. In this embodiment, the second lower frequency portions of each wave excitation burst are used to make time-of-flight measurements, because the wave lengths of the transverse and longitudinal waves are the same as those frequencies in, for example, steel.

In another embodiment, the frequencies are chosen to be the longitudinal and transverse resonant frequencies of the transducer in order to optimize the performance of the transducer for generating both wave types. Frequencies for the two wave types may be selected in order to optimize measurements in specific materials using specific transducers.

It will be appreciated by one skilled in the art that the use of different frequencies for longitudinal and transverse acoustic wave measurements can also be used with other pulse echo measurement techniques to improve measurement accuracy.

Figure 10:
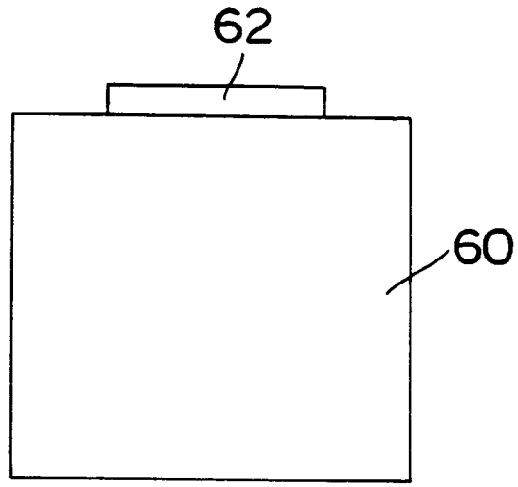
FIG. 10 illustrates a medium having a piezoelectric or electromagnetic transducer removably or permanently attached thereto.
Figure 11:
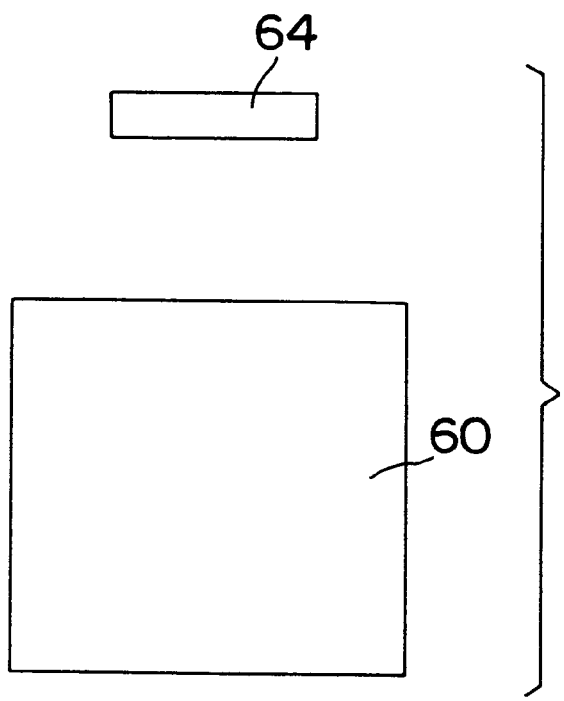
FIG. 11 illustrates a medium having a laser adjacent thereto.

FIGS. 10 and 11 show a medium 60 through which the time-of-flight of ultrasonic signals are measured according to a method of the present invention. The ultrasonic waves are transmitted and received, for example, by a piezoelectric or an electromagnetic transducer 62 removably or permanently attached to medium 60 (see FIG. 10), or a laser 64 adjacent medium 60 (see FIG. 1).

The above-described invention sets forth these and other advantages over the prior art. For example, the invention substantially improves the robustness and accuracy of systems relying on TOF measurements by eliminating a source of ambiguity in making such measurements. Also, it makes possible the measurement of load in a sample based on the knowledge of the absolute (described above) longitudinal and transverse times-of-flight through the sample, and eliminates problems caused by sudden increases in the TOF which occur when using impulse and impact tools. Further, the invention may be readily implemented in an algorithm suitable for automation.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A method of measuring in a material a time-of flight of a signal, said method comprising:

(a) transmitting into the material a signal having a predetermined fixed frequency, said signal having a first signal burst and a second signal burst, and said first signal burst having a first set of cycles and said second signal burst having a second set of cycles;

(b) identifying a cycle in said second set of cycles in said second signal burst corresponding to a cycle in said first set of cycles in said first signal burst; and (c) subtracting the time-of-flight of said identified cycle in said first signal burst from the time-of-flight of said identified cycle in said second signal burst, to measure the time-of-flight of the signal.

2. A method of measuring in a material a time-of-flight of a first signal through the material using a second signal, said method comprising:

(a) measuring times-of-flight of said first signal having a first predetermined fixed frequency and said second signal having a second predetermined fixed frequency different from said first predetermined fixed frequency; and (b) identifying times-of-flight in said first signal and said second signal which are independent of frequency.

3. A method according to claim 1, wherein said step of identifying corresponding cycles on said first signal burst and said second signal burst comprises the steps of:

(a) applying to the material a first signal having a first signal burst and a second signal burst, wherein said first signal burst has a first set of cycles and said second signal burst has a second set of cycles corresponding to said first set of cycles and said first signal has a first frequency;

(b) collecting a first set of times-of-fight, relative to an arbitrary point in time, for each cycle of said first set of cycles of said first signal burst and each cycle from said second set of corresponding cycles of said second signal burst;

(c) calculating first difference absolute values between said times-of-flight of each cycle in said first set of cycles in said first signal burst and each cycle in said second set of corresponding cycles in said second signal burst;

(d) applying to the material a second signal having a third signal burst and a fourth signal burst, wherein said third signal burst has a third set of cycles and said fourth signal burst has a fourth set of cycles corresponding to said third set of cycles and wherein said second signal has a second frequency;

(e) collecting a second set of times-of-flight, relative to an arbitrary point in time, for each cycle in said third set of cycles of said third signal burst and each cycle in said fourth set of cycles of said fourth signal burst;

(f) calculating second difference absolute values between said times-of-flight of each cycle in said third set of cycles of said third signal burst and each cycle in said fourth set of cycles of said fourth signal burst;

(g) calculating third difference absolute values between said first difference absolute values and said second difference absolute values;

(h) matching identical and similar third difference values; and (i) identifying the third difference value closest to a predetermined value.

4. A method according to claim 1, wherein said step of identifying corresponding cycles on said first signal burst and said second signal burst comprises the steps of:

(a) applying to the material a first signal, said first signal having a first portion at a first frequency and a second portion at a second frequency different from said first frequency;

(b) aligning a first zero crossing of one cycle of said first signal burst and a second zero crossing of one cycle of said second signal burst;

(c) calculating the absolute values of the differences in time of the zero crossings for each cycle from a first set of remaining cycles of said first signal burst and each cycle from a corresponding second set of remaining cycles of said second signal burst;

(d) summing the absolute values of said differences;

(e) successively shifting said second signal burst one cycle is forward and one cycle backward relative to said alignment of said first zero crossing of one cycle of said first signal burst and said second zero crossing of said second signal burst; and (f) repeating steps (b)–(e) until the lowest cumulative zero crossing time difference of said differences is identified.

5. The method according to claim 4, wherein said first signal is transmitted and received with a transducer selected from the group consisting of piezoelectric and electromagnetic transducers.

6. The method according to claim 4, wherein said first signal is transmitted and received with a laser.

7. The method according to claim 5, wherein said second frequency is a resonant frequency of said transducer.

8. A method of measuring the time-of-flight of a signal in a material, said method comprising the steps of:

(a) transmitting a signal burst into the material with an ultrasonic signal transmitting means, said signal burst having a first portion at a first predetermined fixed frequency and a second portion at a second predetermined fixed frequency different from said first predetermined fixed frequency, and a first set of cycles;

(b) receiving a signal burst having a second set of cycles from the material;

(c) identifying one of said received signal burst cycles corresponding to one of said transmitted signal burst cycles; and (d) calculating said time-of-flight by subtracting the time of said transmitted signal burst cycle from the time of said corresponding received signal burst cycle.

9. A method according to claim 8, wherein said signal is an ultrasonic wave.

10. A method according to claim 9, wherein said time-of-flight measurements are made in a load-bearing member and used to determine a measure of load on said load-bearing member.

11. A method according to claim 8, wherein said step of identifying said received signal burst cycle corresponding to said transmitted signal burst cycle comprises the steps of:

(a) determining the times of the zero crossings of said transmitted signal burst cycles;

(b) measuring the times of the zero crossings of said received signal burst cycles;

(c) applying a correlation technique to match the zero crossings of said received signal burst with the zero crossings of said transmitted signal burst.

12. A method according to claim 11, wherein said correlation technique comprises:

(a) aligning a first zero crossing of one cycle from a first set of cycles of said transmitted signal burst and a second zero crossing of one cycle from a second set of cycles of said received signal burst, said second set of cycles corresponding to said first set of cycles;

(b) calculating absolute values of the differences in the time of the zero crossings for each remaining cycle of said first set of cycles of said transmitted signal burst and each remaining cycle of said second set of corresponding cycles of said received signal burst;

(c) summing said absolute values of said differences;

(d) successively shifting said received signal burst one cycle forward and one cycle backward relative to said alignment of said first zero crossing of one cycle of said transmitted signal burst and said second zero crossing of said received signal burst; and (e) repeating steps (a)–(d) until a lowest cumulative zero crossing time difference of said differences is identified.

13. A method according to claim 8, wherein said second frequency of said second portion of said transmitted signal burst is a natural resonant frequency of said signal transmitting means.

14. A method according to claim 8, wherein said signal transmitting means is a transducer selected from the group consisting of piezoelectric and electromagnetic transducers.

15. A method according to claim 8, wherein said signal transmitting means is a laser.

16. A method of independently measuring the times-of-flight of a longitudinal ultrasonic wave and a transverse ultrasonic wave in a material, said method comprising:

(a) transmitting into the material said longitudinal and transverse ultrasonic waves at at least two different frequencies with one ultrasonic transmitting means, (b) measuring the time-of-flight of said longitudinal ultrasonic wave with a first signal at a first predetermined fixed frequency, and (c) measuring the time-of-flight of said transverse ultrasonic wave with a second signal at a second predetermined fixed frequency.

17. A method according to claim 16, wherein said time-of-flight measurements are made in a load-bearing member and used to determine a measure of load on said load bearing member.

18. A method according to claim 16, wherein said first frequency and said second frequency are chosen such that a wavelength of said longitudinal ultrasonic wave in the material produced by said first frequency is approximately equal to a wavelength of said transverse ultrasonic wave in the material produced by said second frequency.

19. A method according to claim 16, wherein said first frequency is chosen to be approximately a longitudinal wave resonant frequency of said transmitting means and said second frequency is chosen to be approximately a transverse wave resonant frequency of said transmitting means.

20. A method according to claim 16, wherein said ultrasonic signal transmitting means is selected from the group consisting of piezoelectric and electromagnetic transducers.

21. A method according to claim 16, wherein said ultrasonic signal transmitting means is a laser.

22. A method according to claim 1, wherein said signal is an ultrasonic wave.

23. A method according to claim 2, wherein said first and second signals are ultrasonic waves.

24. A method according to claim 1, wherein said signal is transmitted with an ultrasonic signal transmitting means selected from the group consisting of piezoelectric and electromagnetic transducers.

25. A method according to claim 2, wherein said first and second signals are transmitted with an ultrasonic signal transmitting means selected from the group consisting of piezoelectric and electromagnetic transducers.

26. A method of measuring in a material a time-of flight of a signal, said method comprising:

(a) transmitting a signal having a first signal burst and a second signal burst into the material, said first signal burst having a first set of cycles and said second signal burst having a second set of cycles;

(b) identifying a cycle in said second set of cycles in said second signal burst corresponding to a cycle in said first set of cycles in said first signal burst; and (c) subtracting the time-of-flight of said identified cycle in said first signal burst from the time-of-flight of said identified cycle in said second signal burst, to measure the time-of-flight of the signal, wherein said step of identifying corresponding cycles on said first signal burst and said second signal burst comprises the steps of:

(d) applying to the material a first signal having a first signal burst and a second signal burst, and said first signal burst has a first set of cycles and said second signal burst has a second set of cycles corresponding to said first set of cycles and said first signal has a first frequency;

(e) collecting a first set of times-of-flight, relative to an arbitrary point in time,, for each cycle of said first set of cycles of said first signal burst and each cycle from said second set of corresponding cycles of said second signal burst;

(f) calculating first difference absolute values between said times-of-flight of each cycle in said first set of cycles in said first signal burst and each cycle in said second set of corresponding cycles in said second signal burst;

(g) applying to the material a second signal having a third signal burst and a fourth signal burst, wherein said third signal burst has a third set of cycles and said fourth signal burst has a fourth set of cycles corresponding to said third set of cycles and said second signal has a second frequency;

(h) collecting a second set of times-of-flight, relative to an arbitrary point in time, for each cycle in said third set of cycles of said third signal burst and each cycle in said fourth set of cycles of said fourth signal burst;

(i) calculating second difference absolute values between said times-of-flight of each cycle in said third set of cycles of said third signal burst and each cycle in said fourth set of cycles of said fourth signal burst;

(j) calculating third difference absolute values between said first difference absolute values and said second difference absolute values;

(k) matching identical and similar third difference values; and (l) identifying the third difference values closest to a predetermined value.

27. A method of measuring in a material a time-of flight of a signal, said method comprising:

(a) transmitting a signal having a first signal burst and a second signal burst into the material, said first signal burst having a first set of cycles and said second signal burst having a second set of cycles;

(b) identifying a cycle in said second set of cycles in said second signal burst corresponding to a cycle in said first set of cycles in said first signal burst; and (c) subtracting the time-of-flight of said identified cycle in said first signal burst from the time-of-flight of said identified cycle in said second signal burst, to measure the time-of-flight of the signal, wherein said step of identifying corresponding cycles on said first signal burst and said second signal burst comprises the steps of:

(d) applying to the material a first signal, said first signal having a first portion at a first frequency and a second portion at a second frequency different from said first frequency;

(e) aligning a first zero crossing of one cycle of said first signal burst and a second zero crossing of one cycle of said second signal burst;

(f) calculating the absolute values of the differences in time of the zero crossings for each cycle from a first set of remaining cycles of said first signal burst and each cycle from a corresponding second set of remaining cycles of said second signal burst;

(g) summing the absolute values of said differences;

(h) successively shifting said second signal burst one cycle forward and one cycle backward relative to said alignment of said first zero crossing of one cycle of said first signal burst and said second zero crossing of said second signal burst; and (i) repeating steps (e)–(h) until the lowest cumulative zero crossing time difference of said differences is identified.

28. A method according to claim 27, wherein said first signal is transmitted and received with a transducer selected from the group consisting of piezoelectric and electromagnetic transducers.

29. A method according to claim 27, wherein said first signal is transmitted and received with a laser.

30. A method according to claim 28, wherein said second frequency is a resonant frequency of said transducer.

* * * * *